United States Patent
Ma

(10) Patent No.: US 10,252,961 B2
(45) Date of Patent: Apr. 9, 2019

(54) ONE VESSEL PROCESS FOR MAKING 1,2-PROPANEDIOL FROM A HIGH FRUCTOSE FEEDSTOCK

(71) Applicant: Archer Daniels Midland Company, Decatur, IL (US)

(72) Inventor: Chi Cheng Ma, Forsyth, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 15/548,034

(22) PCT Filed: Feb. 2, 2016

(86) PCT No.: PCT/US2016/016116
§ 371 (c)(1),
(2) Date: Aug. 1, 2017

(87) PCT Pub. No.: WO2016/126671
PCT Pub. Date: Aug. 11, 2016

(65) Prior Publication Data
US 2018/0016214 A1  Jan. 18, 2018

Related U.S. Application Data

(60) Provisional application No. 62/111,190, filed on Feb. 3, 2015.

(51) Int. Cl.
*C07C 29/132* (2006.01)
*B01J 23/89* (2006.01)
*B01J 37/02* (2006.01)
*B01J 37/18* (2006.01)
*C07C 29/60* (2006.01)
*B01J 37/20* (2006.01)
*B01J 21/18* (2006.01)

(52) U.S. Cl.
CPC .............. *C07C 29/132* (2013.01); *B01J 21/18* (2013.01); *B01J 23/892* (2013.01); *B01J 23/8926* (2013.01); *B01J 37/0215* (2013.01); *B01J 37/0236* (2013.01); *B01J 37/18* (2013.01); *B01J 37/20* (2013.01); *C07C 29/60* (2013.01); *Y02P 20/52* (2015.11)

(58) Field of Classification Search
CPC ........... C07C 29/60; B01J 23/72; B01J 27/04
See application file for complete search history.

(56) References Cited

U.S. PATENT DOCUMENTS

| | | | |
|---|---|---|---|
| 4,430,253 A * | 2/1984 | Dubeck | B01J 23/462 502/185 |
| 8,227,646 B2 * | 7/2012 | Tuck | C07C 29/60 568/861 |
| 2005/0266135 A1 * | 12/2005 | Silver | A23G 1/40 426/548 |

* cited by examiner

*Primary Examiner* — Rosalynd A Keys
(74) *Attorney, Agent, or Firm* — William B. Miller

(57) ABSTRACT

A process is described for directly converting a high fructose feedstock to a product mixture including one or more lower polyols in which 1,2-propanediol is produced in preference to any other lower polyols, wherein a high fructose feed and a source of hydrogen are supplied to a reaction vessel and reacted in the presence of a copper-containing, supported ruthenium catalyst to provide the product mixture.

10 Claims, No Drawings

US 10,252,961 B2

ONE VESSEL PROCESS FOR MAKING 1,2-PROPANEDIOL FROM A HIGH FRUCTOSE FEEDSTOCK

TECHNICAL FIELD

The present invention relates generally to processes for making biobased propylene glycol (1,2-propanediol), and more particularly, to processes for making biobased propylene glycol from sugars.

BACKGROUND ART

Propylene glycol is an industrially important commodity chemical which until recently has been made only downstream of conventional fossil fuel operations. As a result of significant research efforts, however, biobased propylene glycol is now commercially available.

Such biobased, renewably sourced materials can be differentiated from their petroleum-derived counterparts, for example, by their carbon isotope ratios using ASTM International Radioisotope Standard Method D 6866, the disclosure of which is incorporated by reference in its entirety. Method D 6866 is based upon the fact that isotopic ratios of the isotopes of carbon within any given material, such as the 13C/12C carbon isotopic ratio or the 14C/12C carbon isotopic ratio, can be determined using certain established analytical methods, such as isotope ratio mass spectrometry, with a high degree of precision.

ASTM Method D 6866, similar to radiocarbon dating, compares how much of a decaying carbon isotope remains in a sample to how much would be in the same sample if it were made of entirely recently grown materials. The percentage is called the biobased content of the product. Samples are combusted in a quartz sample tube and the gaseous combustion products are transferred to a borosilicate break seal tube. In one method, liquid scintillation is used to count the relative amounts of carbon isotopes in the carbon dioxide in the gaseous combustion products. In a second method, 13C/12C and 14C/12C isotope ratios are counted (14C) and measured (13C/12C) using accelerator mass spectrometry. Zero percent 14C indicates the entire lack of 14C atoms in a material, thus indicating a fossil (for example, petroleum based) carbon source. One hundred percent 14C, after correction for the post-1950 bomb injection of 14C into the atmosphere, indicates a modern carbon source. ASTM D 6866 effectively distinguishes between biobased materials and petroleum derived materials in part because isotopic fractionation due to physiological processes, such as, for example, carbon dioxide transport within plants during photosynthesis, leads to specific isotopic ratios in natural or biobased compounds. By contrast, the 13C/12C carbon isotopic ratio of petroleum and petroleum derived products is different from the isotopic ratios in natural or bioderived compounds due to different chemical processes and isotopic fractionation during the generation of petroleum. In addition, radioactive decay of the unstable 14C carbon radioisotope leads to different isotope ratios in biobased products compared to petroleum products. As used herein, "biologically derived", "bioderived", and "biobased" may be used interchangeably to refer to materials whose carbon content is shown by ASTM D 6866, in whole or in significant part (for example, at least about 20 percent or more), to be derived from or based upon biological products or renewable agricultural materials (including but not limited to plant, animal and marine materials) or forestry materials.

Processes have been developed through the aforementioned research efforts to make a biobased propylene glycol both from glycerol as produced as a byproduct in the manufacture of biodiesel, as well as to make biobased propylene glycol from sugars. The availability of a reasonably affordable glycerol feedstock however depends on a strong global demand for biodiesel, and biodiesel process economics and demand have been affected by changing regulatory environments and governmental programs and initiatives, so that processes to make biobased propylene glycol from sugars have been the subject of significant research work.

The processes that have been proposed in the art as a consequence of this significant research work have almost all involved a plurality of steps. In a first step, for example, in a typical process for converting dextrose or fructose to a biobased propylene glycol, conventionally the six carbon sugar is first hydrogenated to a six carbon sugar alcohol such as sorbitol, and then the sorbitol undergoes a separate hydrogenolysis step (typically in a second reactor) under a second set of conditions to yield lower molecular weight polyols inclusive of propylene glycol.

U.S. Pat. No. 7,038,094 to Werpy et al., for example, describes the conversion of six carbon chain sugar alcohols such as sorbitol to polyols inclusive of propylene glycol, using a multimetallic rhenium-containing catalyst. Other references of a similar nature but using different catalyst systems include U.S. Pat. Nos. 5,206,927, 4,476,331, and European Patent Applications EP-A-0523 014 and EP-A-0 415 202, though many other examples could be cited without difficulty.

One notable such example is U.S. Pat. No. 4,430,253 to Dubeck et al. ("Dubeck"), which describes a process for the production of a lower polyhydric alcohol or a mixture thereof by the hydrogenation and hydrogenolysis of a carbohydrate in two stages. The first stage hydrogenation produces higher polyhydric alcohols such as sorbitol, wherein the catalyst may be a "well-known hydrogenation catalyst". Examples given include ruthenium, nickel, cobalt and copper catalysts, with ruthenium on carbon catalysts specifically named along with copper on alumina and copper chromite catalysts. In the second stage, the higher polyhydric alcohols undergo hydrogenolysis to desirable lower polyhydric alcohols; sorbitol, for example, is converted to ethylene glycol and propylene glycol. A preferred catalyst for the second stage conversion of sorbitol to ethylene glycol and propylene glycol is a sulfide-modified ruthenium catalyst. In one embodiment that is described, a ruthenium on carbon catalyst used for the first stage hydrogenation is sulfide-modified by the addition of a sulfide-containing solution, typically following the introduction also of a base promoter such as calcium oxide. In another embodiment, the sulfide modified ruthenium catalyst can be "completely prepared prior to the addition of the polyhydric alcohol solution," col. 7, lines 53-55.

A couple of examples of single-step processes may, however, be found in the literature. In Zhou et al., "Selective Production of 1,2-Propylene Glycol from Jerusalem Artichoke Tuber Using Ni—$W_2C$/AC Catalysts", ChemSusChem 2012, vol. 5, pp. 932-938 (2012), Zhou et al. referenced as background a 2006 study by Fukuoka et al. wherein a single vessel process was described for accomplishing the hydrolysis of cellulose to provide hexose sugars and the hydrogenation of those sugars to the corresponding hexitols, and then proceeded to describe their discovery of a process for accomplishing the hydrolysis of cellulose, the breaking (cracking) of C—C bonds of the hexoses, and hydrogenation of these hexose hydrogenolysis products to provide ethylene glycol and propylene glycol. Where the predominant hexose obtained from the biomass was glucose (or dextrose), ethylene glycol was found to be the main product, whereas the processing of the inulin-based Jerusalem artichoke biomass was said to provide propylene glycol as the main product. Under optimized conditions, the maximum yield of propylene glycol was reported to be as high as 38.5%, with a combined yield of EG and PG of 52.6%. The catalyst used by Zhou et al. was described as a nickel promoted $W_2C$ on activated carbon (AC) catalyst, with the best results reported with a 4% Ni-20% $W_2C$/AC catalyst at 245 degrees Celsius, 6 MPa hydrogen and a reaction time of 80 minutes.

The nickel was found to be necessary to catalyze the hydrogenation of acetol; however, the nickel was also found to promote sintering so that a balancing of positive and negative effects was indicated. Other transition metals such as Pt and Ru were found in substitution of nickel to produce a significant amount of hexitols but no acetol and significantly lower propylene glycol yields. Activated nickel supported Ni nanoparticle catalysts were also found to be effective for both the C—C cracking of sugars and for the hydrogenation of acetol to propylene glycol, though nickel-promoted $W_2C$ catalysts were described as exhibiting a synergistic effect as compared to nickel or $W_2C$ catalysts alone.

The capacity to make biobased propylene glycol from a high fructose feedstock is of considerable commercial interest since high fructose syrups are commercially made and used as sweeteners throughout the world under various customary names—being commonly referenced as high fructose corn syrup (HFCS) in the United States, glucose-fructose in Canada, isoglucose, glucose-fructose syrup or fructose-glucose syrup in Europe and as high fructose maize syrup in some countries. Nevertheless, in recent years such syrups have been identified by some as contributing to a tendency toward obesity as well as blamed for a number of other adverse health effects, so that a simple, one-step process for converting a high fructose feedstock to a biobased propylene glycol would be extremely desirable—and especially if the process were well-adapted to make efficient use of the high fructose streams or products that are currently available, so that in the event of a decreased sweetener demand, an alternative beneficial use can be made of these with a minimum of additional effort and expense.

HFCS in this regard consists of 24% water and the rest sugars. The most widely used varieties of HFCS are: HFCS 55 (mostly used in soft drinks), approximately 55% fructose and 42% glucose; and HFCS 42 (used in beverages, processed foods, cereals, and baked goods), approximately 42% fructose and 53% glucose. HFCS-90, approximately 90% fructose and 10% glucose, is also commercially used as a product in small quantities for specialty applications, but primarily is found in current production as a blendstock with HFCS 42 to make HFCS 55. Consequently, a "high fructose feedstock" for purposes of the present invention will be understood as including mixtures of fructose with one or more additional sugars wherein the fructose is at least about 42 percent by weight of the sugars as a whole.

SUMMARY OF THE INVENTION

The present invention in one aspect concerns a one-step process for directly converting a high fructose feedstock to a product mixture including one or more lower polyols in which 1,2-propanediol is produced in preference to any other lower polyols, wherein a high fructose feed and a source of hydrogen are supplied to a reaction vessel and reacted in the presence of a copper-containing, supported ruthenium catalyst to provide the product mixture. "Lower polyols" in this context and as used herein refers to polyols having fewer than six carbon atoms, and typically includes the ethylene glycol, glycerol and butanediol products that have been associated with previous sorbitol hydrogenolysis processes.

In certain embodiments, the high fructose feed is of a character consistent with a commercial HFCS 42 sweetener product, being comprised of about 42% fructose and about 53% glucose.

In certain embodiments, the high fructose feed is of a character consistent with a commercial HFCS 55 sweetener product, being comprised of about 55% fructose and about 42% glucose.

In certain embodiments, the high fructose feed is of a character consistent with a commercial HFCS 90 sweetener product, comprised of about 90% fructose and about 10% glucose.

In certain embodiments, the high fructose feed is comprised of the hydrogenolysis product of a fructose-containing biomass, such as the Jerusalem artichoke.

In certain embodiments, the high fructose feed is comprised of fructose with one or more additional sugars wherein the fructose is at least 42 percent by weight of the combined sugars in the feed.

In certain embodiments, the catalyst comprises sulfided ruthenium and copper on a support. In this aspect, we have discovered that a catalyst of the type generally described by Dubeck, when modified by addition of copper, can be used for a single stage conversion from high fructose feeds directly to propylene glycol and other lower polyols and without the necessity of added base. Dubeck does teach that the carbohydrate can be fructose or can be "in particular" a mixture of glucose and fructose, see col. 4, lines 6-10, but all of Dubeck's examples are of a two-stage process and with dextrose only.

In certain embodiments, the high fructose feedstock is supplied to the process both at the beginning of a continuous or semibatch process, and at one or more locations downstream of the reactor inlet in a continuous process or at one or more later addition times in a semibatch process, for approaching but not substantially exceeding an optimized fructose concentration (which will usually correspond to the inlet or beginning concentration of fructose in the feed) along at least some portion of the length (meaning, in the axial flow direction to the product outlet) of a reactor in the continuous process, or for a longer period of time in the semibatch process.

In this regard, as further explained in our published application WO 2015/119767, solid catalysts are desirably used in gas-liquid reaction systems for facilitating the separation and recovery of spent catalyst and the processing of crude reaction products, but gas-liquid reaction systems frequently pose difficulties in terms of getting a gaseous reactant into a liquid and to a heterogeneous solid catalyst surface. As a result, in certain types of low-mixing multi-phase processes particularly, substoichiometric gas to liquid reactant ratios can occur in the presence of the catalyst, so that undesirable side reactions can be catalyzed of liquid phase components at the solid catalyst interface. As well, replenishment of the gas reactant(s) is difficult as the gas reactant(s) is spent in these undesirable side reactions. Further, catalyst lifetime can be shortened by the interaction of the liquid reactant(s) with the catalyst.

We found in the referenced application, briefly, that by selecting an optimized substrate concentration in the feedstock (considering such factors as catalyst deactivation rates, byproduct formation and related purification requirements, productivity in terms of desired products and selectivity to those products and so forth), and then seeking to substantially perpetuate this optimized concentration along at least some portion of the length of a multiphase low mixing gas-liquid reaction system, or for a longer period of time in a semibatch, multiphase low mixing process, substantial improvements in productivity and throughput could be realized even given feedstock concentration limitations (in this instance as in many others) necessitated by solubility and mass transfer limitations of hydrogen in the high fructose feedstock.

DESCRIPTION OF EMBODIMENTS

As earlier mentioned, a context of use for the present invention that is especially of interest is in the conversion of currently-manufactured high fructose syrups to 1,2-propanediol, an important commodity chemical that has historically been made from non-renewable resources and that has only recently been manufactured commercially from biobased, renewable resources. Such high fructose syrups are commercially made and used as sweeteners throughout the world under various customary names—being commonly referenced as high fructose corn syrup (HFCS) in the United States, glucose-fructose in Canada, isoglucose, glucose-fructose syrup or fructose-glucose syrup in Europe and as high fructose maize syrup in some countries—but in recent years have been viewed by some as contributing to obesity and a number of other adverse health effects.

In the United States, these high fructose syrups are conventionally made from corn as a starch source and thus identified as high fructose corn syrups (HFCS), and it will be in the context of these commercial HFCS sweetener products that the present detailed description will be presented, though it will be clearly understood that "high fructose feed" or "high fructose feedstocks" as used herein extend to mixtures of fructose with one or more additional sugars wherein the fructose is at least 42 percent by weight of the sugars as a whole however these mixtures are derived—whether from another starch source or from the processing of a biomass, for example but without limitation, a non-food biomass such as the fructose-containing Jerusalem artichoke tuber investigated by Zhou et al.

With this understanding, a preferred application of the present invention will be for the conversion of a high fructose feedstock in the form of a commercial HFCS 90 sweetener product to a product mixture including lower polyols and wherein 1,2-propanediol is produced in preference to any other lower polyols. Even more preferably, 1,2-propanediol is favored over sorbitol as a product.

In one embodiment, HFCS 90 and hydrogen are combined and reacted in the presence of a copper-containing, supported ruthenium catalyst to provide the product mixture. In a preferred embodiment, the catalyst comprises sulfided ruthenium and copper on a support. Carbon is a presently preferred support material.

The process can be carried out in a batch, semi-batch or continuous mode, but preferably will be carried out in a semi-batch or continuous manner according to a method of the type described in our WO 2015/119767 published application, wherein HFCS 90 is combined with an inert solvent and the resultant high fructose feed contains preferably not more than 50 percent by weight of fructose, more preferably contains not more than 30 percent by weight of fructose and still more preferably contains not more than 10 percent by weight of fructose. Thereafter, in a semi-batch method, one or more additions are made of the high fructose feed over time to closely approach and preferably achieve, but not substantially exceed, the initial fructose concentration within the batch. Preferably, by means of one or more subsequent additions of the high fructose feed, the fructose feed concentration within the batch will be maintained on average within 20 percent of the initial fructose concentration over the duration of a batch, more preferably within 10 percent of the initial fructose concentration and still more preferably within 5 percent of the initial fructose concentration over the duration of a batch.

Likewise, in a continuous mode of operation, fructose is introduced (typically in the form of HFCS 90 or in the form of additional of another such high fructose feed) at a plurality of locations in the direction of fluid flow through the reactor toward the product outlet, so as to maintain (or substantially maintain) the inlet fructose concentration along some portion of the length of the reactor. Preferably, over the length of the reactor, the fructose concentration is maintained on average within 15 percent of the inlet fructose concentration, more preferably is maintained within 10 percent of the inlet fructose concentration and still more preferably is maintained within 5 percent of the inlet fructose concentration. The reactor will preferably be a fixed bed reactor of the trickle bed or packed bubble column variety or in a series of such reactors including quench boxes wherein downstream additions of fructose are accomplished, though continuous multiphase, low mixing slurry reactors (transported bed reactors) are contemplated as well.

If conducted in semi-batch mode, batch times are preferably from 1 to 6 hours in duration, more preferably from 1 to 4 hours in length, and still more preferably from 2 to 3 hours in duration, at a reaction temperature of from 50 to 250 degrees Celsius, preferably of from 100 to 250 degrees Celsius and more preferably from 150 to 200 degrees Celsius. Hydrogen will be supplied at a pressure of from 3.5 MPa to 17.5 MPa, gauge (500 to 2500 pounds per square inch, gauge), preferably at a pressure of from 7.0 MPa to 14.0 MPa, gauge (1000 to 2000 psig), and more preferably at a pressure of from 10.5 MPa to 14.0 MPa, gauge (1500 to 2000 psig).

The catalyst is a copper-containing, supported ruthenium catalyst and will preferably comprise from 0.5 to 10.0 weight percent of ruthenium based on the total weight of the catalyst, more preferably from 1.0 to 5.0 weight percent of ruthenium and still more preferably will comprise from 2.0 to 3.0 weight percent of ruthenium with from 1.0 to 20.0 weight percent of the catalyst being copper, more preferably from 1.0 to 10.0 weight percent and still more preferably from 2.0 to 5.0 percent by weight of the catalyst being copper. A catalyst further containing sulfur is further preferred, with sulfur contents ranging from 0.1 to 5.0 percent by weight, more preferably from 0.5 to 2.0 weight percent and still more preferably from 0.5 to 1.0 percent by weight of the catalyst. It should be noted, parenthetically, that the specification of a more preferred Ru content, a more preferred Cu content and a more preferred S content should by no means be taken to imply that values of Ru, Cu and S within broader ranges of preferred weight percentages for one or both of the other components are excluded in combination with a value of a particular component selected within a more preferred range; thus, for example, a Ru content selected within the narrowest range indicated above (from 2.0 to 3.0 weight percent) does not require that the Cu and S contents are correspondingly from within the narrowest ranges indicated for these materials or within the next narrowest range of values.

In a continuous mode of operation, particularly with reference to a fixed bed reactor system, the temperature, hydrogen pressure and catalyst aspects are as specified for the semi-batch mode, but a liquid hourly space velocity ranging from 0.5 to 3.0 hr$^{-1}$, preferably from 0.5 to 2.0 hr$^{-1}$ and more preferably from 0.5 to 1.0 hr$^{-1}$ will be employed.

As reflected in the examples following, the product mixture from the inventive process will generally comprise the hydrogenation product sorbitol as well as materials consistent with the occurrence of both hydrogenolysis and hydrogenation, for example, glycerol, erythritol, 1,2-butanediol, ethylene glycol, propylene glycol (1,2-propanediol) and the like. Again as shown in the examples, with the inventive process propylene glycol can be produced in preference to any other lower polyol, and in certain embodiments can be produced in preference both to sorbitol and the various other lower polyols.

Separation of the propylene glycol from the remainder of the product mixture can be accomplished by a number of known methods, see, for example, U.S. Pat. No. 8,143,458 to Kalagias (azeotropic distillation) and U.S. Pat. No. 8,177,980 to Hilaly et al. (simulated moving bed chromatography), but preferably simple distillation may be employed to recover the propylene glycol.

This invention is further illustrated by the following non-limiting examples:

Examples 1-9

A sulfided ruthenium on carbon catalyst including 2 percent of ruthenium and 1 percent of sulfur based on the total weight of the catalyst was loaded with 5 percent by weight of copper by spraying a copper nitrate solution on the dry sulfided ruthenium catalyst, then drying and reducing the catalyst under hydrogen at 250 degrees Celsius.

This catalyst was loaded into a 30 cubic centimeter fixed bed reactor, and hydrogen was thereafter supplied to the reactor at 12.4 MPa, gauge (1800 pounds per square inch, gauge), at a rate of 0.4 liters per minute, together with a liquid feed comprised of 0.794 percent by weight of dextrose, 5.93 weight percent of fructose, 8 percent by weight of ethanol and the remainder of water. The reactor temperature was 190 degrees Celsius, and the liquid hourly space velocity was 0.7 hr$^{-1}$.

The process was continuously run over a period of two weeks, with product samples being drawn on a number of consecutive days within that timeframe. The results are shown below in Table 1, where Example 1 corresponds to the first of six consecutive daily samples drawn and analyzed by GC/MS. All amounts are reported as percents by total weight.

TABLE 1

| Ex. | Sorb.[a] | Dextrose | Fructose | Eryth[b] | Gly[c] | EG | PG | 1,2-BDO |
|---|---|---|---|---|---|---|---|---|
| (Feed) | | 0.794 | 5.93 | | | | | |
| 1 | 0.829 | | | 0.052 | 1.146 | 0.436 | 1.557 | 0.192 |
| 2 | 0.793 | | | 0.046 | 1.155 | 0.411 | 1.503 | 0.013 |
| 3 | 0.785 | | | 0.044 | 1.133 | 0.405 | 1.492 | 0.195 |
| 4 | 0.758 | | | 0.041 | 1.112 | 0.393 | 1.458 | 0.035 |

TABLE 1-continued

| Ex. | Sorb.[a] | Dextrose | Fructose | Eryth[b] | Gly[c] | EG | PG | 1,2-BDO |
|---|---|---|---|---|---|---|---|---|
| 5 | 0.914 | | | 0.05 | 1.281 | 0.386 | 1.494 | 0.022 |
| 6 | 0.941 | | | 0.048 | 1.305 | 0.377 | 1.529 | 0.196 |

[a]Sorbitol;
[b]Erythritol;
[c]Glycerol;
EG = ethylene glycol,
PG = propylene glycol;
1,2-BDO = 1,2-butanediol Example 7

A sulfided ruthenium on carbon catalyst, an experimental apparatus and the same experimental conditions as used in Examples 1-6 were employed on a high fructose feed comprised of a sugars mixture of 0.1 percent by weight of dextrose and 3.4 percent by weight of fructose, with again 8 percent by weight of ethanol and the remainder of water. A sample of the product taken the next day was analyzed by GC/MS, with the results reported in Table 2.

TABLE 2

| Ex. | Sorb.[a] | Dextrose | Fructose | Eryth[b] | Gly[c] | EG | PG | 1,2-BDO |
|---|---|---|---|---|---|---|---|---|
| (Feed) | | 0.1 | 3.4 | | | | | |
| 7 | 0.65 | | | 0 | 0.74 | 0.20 | 0.97 | 0 |

[a]Sorbitol;
[b]Erythritol;
[c]Glycerol;
EG = ethylene glycol,
PG = propylene glycol;
1,2-BDO = 1,2-butanediol Example 8

A high fructose feed comprised of 3.53 percent by weight of dextrose, 3.56 weight percent of fructose (thus consistent with an HFCS 42 sweetener product) with 8 percent by weight of ethanol and the remainder of water was processed using a sulfided Ru/C catalyst, an experimental apparatus and experimental conditions as in previous examples. Analysis of a product sample drawn the following day yielded the results shown in Table 3.

TABLE 3

| Ex. | Sorb.[a] | Dextrose | Fructose | Eryth[b] | Gly[c] | EG | PG | 1,2-BDO |
|---|---|---|---|---|---|---|---|---|
| (Feed) | | 3.53 | 3.56 | | | | | |
| 8 | 1.58 | | | 0 | 1.07 | 0.46 | 1.30 | 0 |

[a]Sorbitol;
[b]Erythritol;
[c]Glycerol;
EG = ethylene glycol,
PG = propylene glycol;
1,2-BDO = 1,2-butanediol Example 9

A sulfided ruthenium on carbon catalyst including 2 percent of ruthenium and 1 percent of sulfur based on the total weight of the catalyst was loaded into a 30 cubic centimeter fixed bed reactor, and hydrogen was thereafter supplied to the reactor at 12.4 MPa, gauge (1800 pounds per square inch, gauge), at a rate of 0.4 liters per minute, together with a liquid feed including a sugars mixture of 3.2 percent by weight of dextrose and 3.8 weight percent of fructose (thus, consistent with an HFCS 55 sweetener product) with 10 percent by weight of ethanol and the remainder of water. The reactor temperature was 190 degrees Celsius, and the liquid hourly space velocity was 0.7 hr$^{-1}$. Analysis of a product sample taken the following day yielded the results shown in Table 4 as follows.

TABLE 4

| Ex. | Sorb.$^a$ | Dextrose | Fructose | Eryth$^b$ | Gly$^c$ | EG | PG | 1,2-BDO |
|---|---|---|---|---|---|---|---|---|
| (Feed) | | 3.2 | 3.8 | | | | | |
| 9 | 1.43 | | | 0 | 1.16 | 0.36 | 1.45 | 0 |

$^a$Sorbitol;
$^b$Erythritol;
$^c$Glycerol;
EG = ethylene glycol,
PG = propylene glycol;
1,2-BDO = 1,2-butanediol

What is claimed is:

1. A process for converting a high fructose feedstock to a product mixture including one or more lower polyols in which 1,2-propanediol is produced in preference to any other lower polyols in a single stage, wherein a high fructose feed and a source of hydrogen are supplied to a reaction vessel and reacted in the presence of a copper-containing, supported ruthenium catalyst to provide the product mixture.

2. The process of claim 1, wherein the high fructose feed comprises at least 42 percent by weight of fructose.

3. The process of claim 2, wherein the high fructose feed comprises 53 percent by weight of glucose.

4. The process of claim 1, wherein the high fructose feed comprises 55 percent by weight of fructose and 42 percent by weight of glucose.

5. The process of claim 1, wherein the high fructose feed comprises 90 percent by weight of fructose and 10 percent by weight of glucose.

6. The process of claim 1, wherein the high fructose feed is comprised of the hydrogenolysis product of a fructose-containing biomass.

7. The process of claim 1, wherein the copper-containing, supported ruthenium catalyst is a copper-containing, sulfided ruthenium catalyst on a support.

8. The process of claim 7, wherein the support is carbon.

9. The process of any of claims 1-8, conducted as a semi-batch process wherein the high fructose feed is supplied to the reaction vessel at a first concentration and subsequently at one or more later times in the course of a batch at the first or a greater concentration.

10. The process of any of claims 1-8, conducted as a continuous process wherein the high fructose feed is supplied to the reaction vessel at a first concentration and at one or more points along the length of the reaction vessel downstream of the reaction vessel inlet at the first or a greater concentration.

* * * * *